US00PP36891P2

(12) United States Plant Patent
Pavlich

(10) Patent No.: US PP36,891 P2
(45) Date of Patent: Aug. 12, 2025

(54) ***HEUCHERA* PLANT NAMED 'Midnight'**

(50) Latin Name: ***Heuchera* hybrid**
Varietal Denomination: Midnight

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 18/897,542

(22) Filed: Sep. 26, 2024

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
See application file for complete search history.

(56) References Cited

PUBLICATIONS

"Terra Nova Nurseries to debut new introductions, catalog at Cultivate '23," *Lawn & Garden Retailer*, pp. 1-7, Jul. 6, 2023.

*Primary Examiner* — Susan McCormick Ewoldt
(74) *Attorney, Agent, or Firm* — Klarquist Sparkman, LLP

(57) ABSTRACT

A new and distinct *Heuchera* cultivar named 'Midnight' distinguished by its glossy black and purple leaf color, medium-large leaves held on short petioles, red purple flowers on upright flowering stems, excellent performance in sun or shade, medium mounding habit with an excellent crown count, and excellent vigor from spring to fall.

2 Drawing Sheets

Latin name of the genus and species of the plant claimed: *Heuchera* hybrid.

Variety designation: 'Midnight'.

BACKGROUND

The present application relates to a new and distinct cultivar of *Heuchera* named 'Midnight'. The cultivar is also known by its trade name, FOREVER® 'MIDNIGHT'. *Heuchera* is in the family Saxifragaceae. *Heuchera* 'Midnight' originated as a spontaneous mutation from *Heuchera* 'Purple' (U.S. Plant Pat. No. 26,358), identified in a batch of tissue culture plants in Canby, Oregon USA.

SUMMARY

The new *Heuchera* cultivar 'Midnight' is distinguished from other *Heuchera* varieties due to the following unique combination of characteristics:

1. Glossy black and purple leaf color
2. Medium large leaves held on short petioles
3. Red purple flowers on upright flowering stems
4. Excellent performance in sun or shade
5. A medium, mounding habit with an excellent crown count, and
6. Excellent vigor from spring until fall Compared to its parent, the new cultivar has darker purple-black leaves, and darker red purple inflorescence and more crowns.

The new variety is distinct from other known *Heuchera* varieties, for example, 'Obsidian' (U.S. Plant Pat. No. 14,836) and 'Berry Marmalade' (U.S. Plant Pat. No. 23,285). Compared to 'Obsidian', the new cultivar has larger, more undulate leaves that are glossier black, shading to purple. In addition, 'Midnight' has a larger habit and a diminished floral display as compared to 'Obsidian'. Compared to 'Berry Marmalade', the new cultivar has a larger, fuller habit and dark, glossy leaves and larger red purple, rather than white, inflorescence.

The new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oregon, shows that the characteristics described herein come true to form, are firmly fixed, and are established and transmitted through succeeding propagations.

The new cultivar has not been evaluated under all possible environmental conditions and certain characteristics may change with changing environmental conditions (such as photoperiod, temperature, moisture, soil conditions, nutrient availability, or other factors). The phenotype may change with variations in environment without a change in the genotype of the plant.

Color descriptions and other terminology are used in accordance with their ordinary dictionary descriptions, unless the context clearly indicates otherwise. Color descriptions used herein are made with reference to The *Royal Horticultural Society Colour Chart,* $5^{th}$ edition, 2007.

Figure 1:
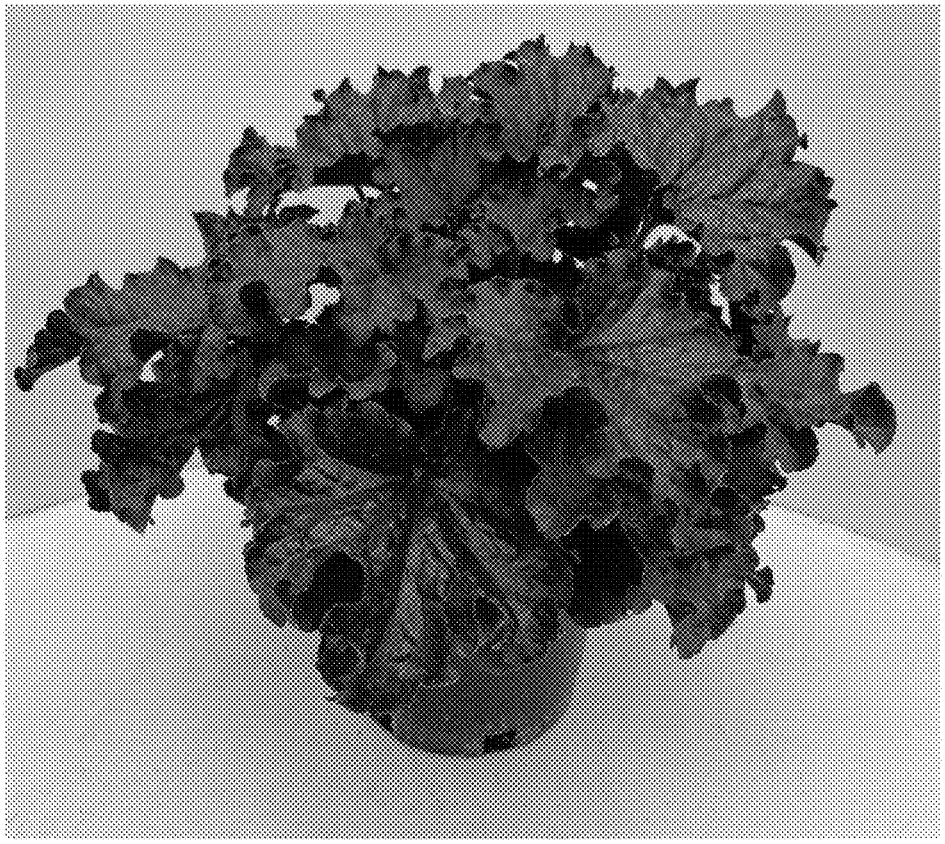
FIG. 1 shows an 8-month-old 'Midnight' plant in a one-gallon container, grown outside in Canby, Oregon.
Figure 2:
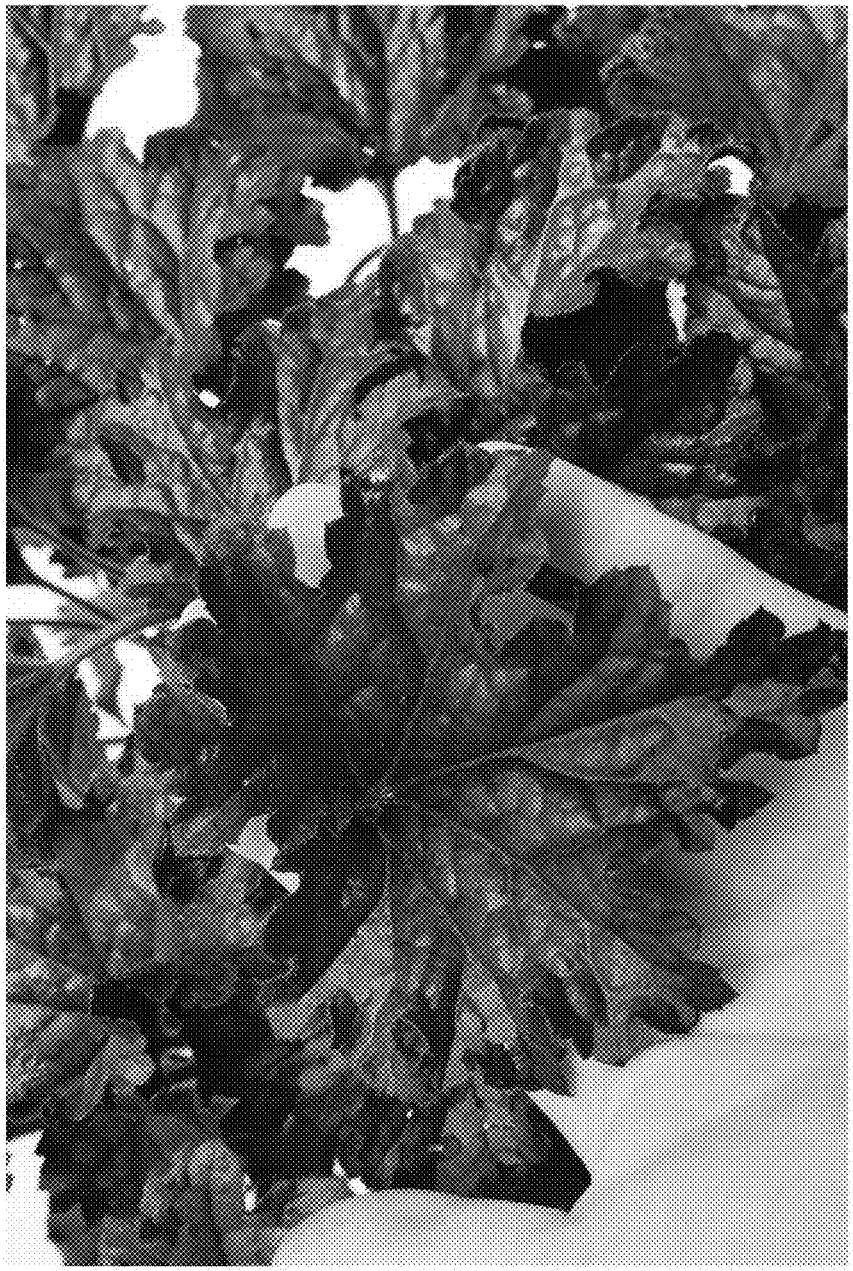
FIG. 2 shows a closeup of 'Midnight' foliage, grown in a greenhouse setting in Canby, Oregon.

The color photographs show typical specimens of the new cultivar and depict the color as nearly true as is reasonably possible. It should be noted that colors may vary, for example due to lighting conditions at the time the photograph is taken. Therefore, color characteristics of this new cultivar should be determined with reference to the observations described herein, rather than from the photograph alone.

DETAILED PLANT DESCRIPTION

The following is a detailed description of the new *Heuchera* cultivar based on observations taken in September of an eight-month-old asexually reproduced progeny grown in a one-gallon pot outdoor in partial shade in Canby, Oregon. Canby is Zone 8 on the USDA Hardiness map. Temperatures range from a high of 95° F. in August to an average of 32° F. in January. Normal rainfall in Canby is 42.8 inches per year.

Plant:

*Form*.—Basal rosette, herbaceous perennial.
*Hardiness*.—USDA Zone 4 to 9.
*Size*.—35 cm tall from top of the foliage to the ground, 45 cm from ground to top of flowers, 40 cm wide.
*Number of crowns*.—About 10.
*Habit*.—Large, mounding.
*Vigor*.—Excellent vigor spring through fall.

Leaf:

*Type*.—Simple.
*Arrangement*.—Rosette.
*Shape*.—Orbicular to ovate.
*Number*.—About 89.
*Blade size*.—Grows to 11 cm long and 11.5 cm wide.
*Venation*.—Palmate.
*Lobing/division*.—Palmately lobed with 6 main lobes with secondary lobes.
*Undulation*.—Moderate.
*Glossiness*.—Medium.
*Margins*.—Broadly crenate.
*Apex*.—Mucronulate.
*Base*.—Cordate, overlapping at sinus.
*Surface texture*.—Sparsely glandular-puberulent on both sides.
*Leaf rugosity*.—Absent.
*Petiole description*.—Grows to 16.5 cm long and 3 mm wide, glandular hairs, 187B.
*Leaf color*.—New leaves: topside and veins are closest to greyed-purple N186A, and highlighted with purple N79B. Mature leaves: mature leaves lose the highlights of purple and appear almost black, closest to greyed-purple N187A. Leaves and veins blend colors to purple N187A as the foliage matures. Bottom side of juvenile and mature leaves are purple N79B.

Inflorescence:

*Size*.—Grows to 5 cm wide and 9.5 cm long.
*Type*.—Upright thyrse.
*Number of flowers per thyrse*.—About 27.
*Flower density*.—Medium to dense.
*Number of thyrse*.—About 7.
*Peduncle*.—Grows to 30 cm long and 4 mm wide at base, glandular hairs, greyed purple N186C.
*Flowering stem attitude*.—Upright.
*Pedicel*.—Grows to 3 mm long, with glandular hairs, N186D.
*Attitude*.—Upright.
*Bloom period*.—Late June through September in Canby, Oregon.

Flower bud:

*Size*.—4 mm wide and 3 mm long.
*Description*.—Glandular-puberulent, ovoid, facing outward.
*Color*.—Red purple 61B.

Flower:

*Type*.—Perfect.
*Shape*.—Campanulate.
*Attitude*.—Outward, slightly downward-facing.
*Size*.—5 mm long and 9 mm wide.
*Corolla description*.—Campanulate, 2 mm long and 1 mm wide; 5 lobes each 1 mm wide and 2 mm long, oblong in shape, back side glandular-puberulent, glabrous inside, tip obtuse, margin entire, outside color red purple 61C on both sides.
*Calyx description*.—Campanulate, 3 mm long and 2 mm wide, spatulate, margins entire, tip acute, glandular-puberulent on back side, glabrous inside, young flowers, red purple 70B on both sides, darkening to red purple 70A at apex. Mature flowers, red purple 73B, darkening to red purple 72B at apex.
*Stamen description*.—5 in number, filaments 1.5 mm long, red purple 65C, anthers 0.5 mm long, greyed-orange 169B, pollen poor, greyed-orange N67B.
*Pistil description*.—1, 2-beaked, 4 mm long and 2 mm wide, red purple 69A overall, ovary 2 mm long and 2 mm wide, style 2 mm long.
*Lastingness*.—Each thyrse blooms for about 3 weeks on the plant.

Fruit:

*Type*.—Two-beaked ovoid capsule.
*Fertility*.—Moderate.
*Color*.—Greyed brown 199A.

Seed:

*Shape*.—Linear.
*Size*.—2 mm long.
*Color*.—Black 202A.

Pest and disease tolerance: The new cultivar is typical to the genus. No known resistance to pests or diseases. No problems have been found in Canby, Oregon.

I claim:

1. A new and distinct *Heuchera* plant named 'Midnight' substantially as illustrated and described herein.

* * * * *